US 6,379,306 B1

(12) United States Patent
Washburn et al.

(10) Patent No.: US 6,379,306 B1
(45) Date of Patent: *Apr. 30, 2002

(54) ULTRASOUND COLOR FLOW DISPLAY OPTIMIZATION BY ADJUSTING DYNAMIC RANGE INCLUDING REMOTE SERVICES OVER A NETWORK

(75) Inventors: Michael J. Washburn, New Berlin; Gary E. MacLeod, Menomonee Falls; Sean D. Lucas, Waukesha; David J. Muzilla, Mukwonago, all of WI (US)

(73) Assignee: General Electric Company, Schenectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/472,048

(22) Filed: Dec. 27, 1999

Related U.S. Application Data

(63) Continuation-in-part of application No. 09/224,342, filed on Dec. 31, 1998, now Pat. No. 6,126,605.

(51) Int. Cl.⁷ .............................................. A61B 8/02
(52) U.S. Cl. ...................................................... 600/454
(58) Field of Search ................... 600/437–454, 600/458; 367/87, 7, 11; 73/574, 625, 626; 348/222; 382/107, 110, 124, 130, 254

(56) References Cited

U.S. PATENT DOCUMENTS 5,997,478 A * 12/1999 Jackson et al. .............. 600/437
6,126,605 A * 10/2000 Washburn et al. .......... 600/454
6,149,597 A * 11/2000 Kamiyama .................. 600/458

* cited by examiner

Primary Examiner—Marvin M. Lateef
Assistant Examiner—Ali M. Imam
(74) Attorney, Agent, or Firm—McAndrews, Held & Malloy, Ltd.; Peter J. Vogel; Michael A. Dellapenna

(57) ABSTRACT

An ultrasound imaging system generating color flow signals in response to ultrasound signals backscattered from a subject under study includes an apparatus for displaying images in response to the color flow signals. The apparatus includes a memory connected to store first memory values in response to the color flow signals; a logic unit connected to determine a dynamic range compression scheme based on an analysis of the first memory values and to generate second memory values based on the dynamic range compression scheme; a display connected to display a color flow image in response to the second memory values; and a network connectivity module coupled to the system to provide communication with a remote facility over a network, the remote facility providing remote services.

21 Claims, 8 Drawing Sheets

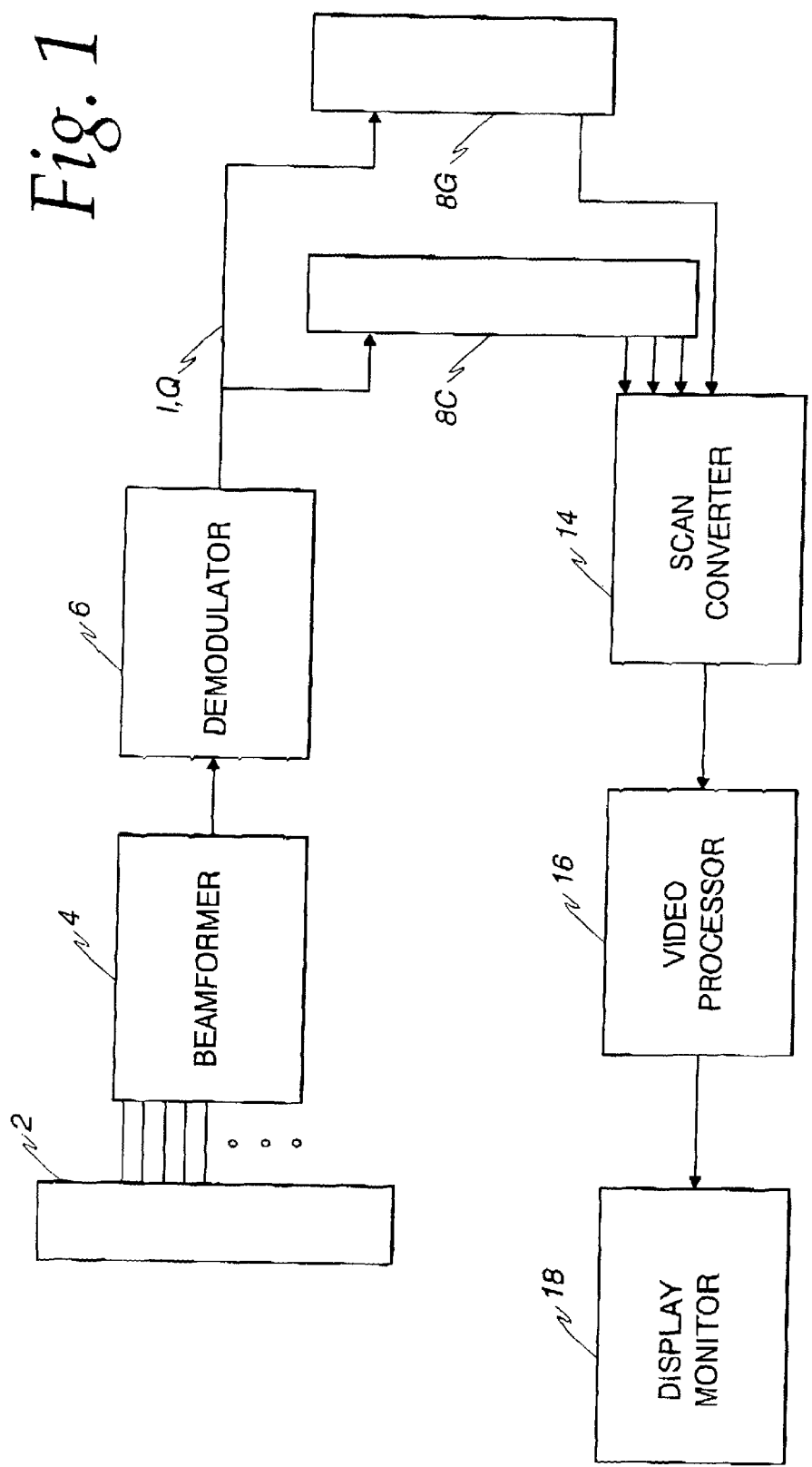

ULTRASOUND COLOR FLOW DISPLAY OPTIMIZATION BY ADJUSTING DYNAMIC RANGE INCLUDING REMOTE SERVICES OVER A NETWORK

CROSS-REFERENCE TO RELATED APPLICATIONS

This application is a continuation-in-part (CIP) of U.S. patent application Ser. No. 09/224,342, entitled "Ultrasound Color Flow Display Optimization By Adjusting Dynamic Range" by Michael J. Washburn et al. filed on Dec. 31, 1998, now U.S. Pat. No. 6,126,605.

BACKGROUND OF THE INVENTION

The present invention relates generally to the field of medical diagnostic systems, such as imaging systems. More particularly, the invention relates to a system and technique for ultrasound color flow Doppler imaging of fluid flow fields.

Ultrasonic scanners for detecting blood flow based on the Doppler effect are known. Such systems operate by actuating an ultrasonic transducer array to transmit ultrasonic waves into the object and receiving ultrasonic echoes backscattered from the object. In the measurement of blood flow characteristics, returning ultrasonic waves are compared to a frequency reference to determine the frequency shift imparted to the returning waves by flowing scatterers such as blood cells. This frequency, i.e., phase shift, translates into the velocity of the blood flow. The blood velocity is calculated by measuring the phase shift from firing to firing at a specific range gate.

The change or shift in backscattered frequency increases when blood flows toward the transducer and decreases when blood flows away from the transducer. Color flow images are produced by superimposing a color image of the velocity of moving material, such as blood, over a black and white anatomical B-mode image. Typically, color flow mode displays hundreds of adjacent sample volumes simultaneously, all laid over a B-mode image and color-coded to represent each sample volume's velocity.

Typically, color flow processors estimate blood flow velocity, blood flow power, and blood flow variance. Typically, color flow data is used to modify the color of a region of interest on a display screen. The user selects the type of data used for the display. The modes typically available are power only, velocity only or velocity and variance combined.

In current ultrasound scanners, various color flow display parameters are either fixed with no user selectability or are preset to some specific setting and can only be changed if action is taken by the user, one parameter at a time. This limits image quality and user productivity for any given application and scanning situation. There is a need for a scanner in which these same parameters can all be automatically adjusted at the same time to optimize image quality related to color flow display for a specific scanning situation, thus increasing user productivity.

In the color flow power mode of operation, known ultrasound scanners typically provide a color flow dynamic range based on a compression curve preselected at the factory depending on the type of scanning application. For example, one dynamic range based on one compression curve is selected for scanning of the kidney, whereas another dynamic range based on another compression curve is selected for scanning of the carotid artery. Frequently, the actual scan data has a dynamic range different from the range upon which the compression curve is based. As a result, the dynamic range of the display is less than optimal. Accordingly, there is a need for a color flow ultrasound scanner which can automatically adjust for changes in the dynamic range of the received signals.

Solutions to the problems described above have not heretofore included significant remote capabilities. In particular, communication networks, such as, the Internet or private networks, have not been used to provide remote services to such medical diagnostic systems. The advantages of remote services, such as, remote monitoring, remote system control, immediate file access from remote locations, remote file storage and archiving, remote resource pooling, remote recording, remote diagnostics, and remote high speed computations have not heretofore been employed to solve the problems discussed above.

Thus, there is a need for a medical diagnostic system which provides for the advantages of remote services and addresses the problems described above. In particular, there is a need for remote upgrades, remote diagnostics, remote servicing, remote viewing, remote file storage, remote control, and remote adjustments to system parameters and functions. Furthermore, there is a need for contractual arrangements, such as, per use licenses which lease the medical diagnostic equipment based on use. Additionally, remote services may include expert on-line assistance for image scanning techniques, image analysis, pathology detection, imaging unit maintenance, and other expert-aided operations.

SUMMARY OF THE INVENTION

One embodiment of the invention relates to an apparatus for displaying images in response to color flow signals in an ultrasound imaging system which generates color flow signals in response to ultrasound signals backscattered from a subject under study. The apparatus includes a memory connected to store first memory values in response to the color flow signals; a logic unit connected to determine a dynamic range compression scheme based on an analysis of the first memory values and to generate second memory values based on the dynamic range compression scheme; a display connected to display a color flow image in response to the second memory values; and a network connectivity module coupled to the system to provide communication with a remote facility over a network, the remote facility providing remote services.

Another embodiment of the invention relates to an improved method for displaying images in response to the color flow signals in an ultrasound imaging system which generates color flow signals in response to ultrasound signals backscattered from a subject under study. The method includes storing first memory values in response to the color flow signals; determining a dynamic range compression scheme based on an analysis of the first memory values; generating second memory values based on the dynamic range compression scheme; displaying a color flow image in response to the second memory values; and communicating the color flow image or data associated with the image to a remote facility, the remote facility providing remote services over a network.

Other principle features and advantages of the present invention will become apparent to those skilled in the art upon review of the following drawings, the detailed description, and the appended claims.

BRIEF DESCRIPTION OF THE DRAWINGS

Preferred exemplary embodiments are described below with reference to the accompanying drawings wherein like reference numerals denote lake elements and:

FIG. 1 is a schematic block diagram showing the signal processing chain for a conventional color flow and B-mode ultrasound imaging system;

DETAILED DESCRIPTION OF THE PREFERRED EMBODIMENT

Referring to FIG. 1, the basic signal processing chain for a color flow and gray scale imaging system comprises an ultrasound transducer array 2, which is activated to transmit pulse sequences comprising tone bursts of length P which are fired repeatedly at a pulse repetition frequency (PRF) which typically is in the kilohertz range. The pulse sequences, including burst lengths P, are different for the color flow and B-mode processing. For color flow imaging, P may be 4 to 8 cycles, and the tone bursts are focused at the same transmit focal position with the same transmit characteristics.

A series of color flow transmit firings focused at the same transmit focal position are referred to as a "packet". Each transmit beam propagates through the object being scanned and is reflected by ultrasound scatterers in the object.

The return RF signals are detected by the transducer elements and received by the respective receive channels in the beamformer 4. The beamformer sums the delayed channel data and outputs in a beam summed signal which is demodulated into in-phase and quadrature (I/Q) signal components by a demodulator 6. The B-mode I, Q outputs from demodulator 6 are transmitted to a mid processor 8G for gray scale B-mode processing, and the color flow 1, Q outputs from demodulator 6 are transmitted to a mid-processor 8C for color processing.

Figure 2:
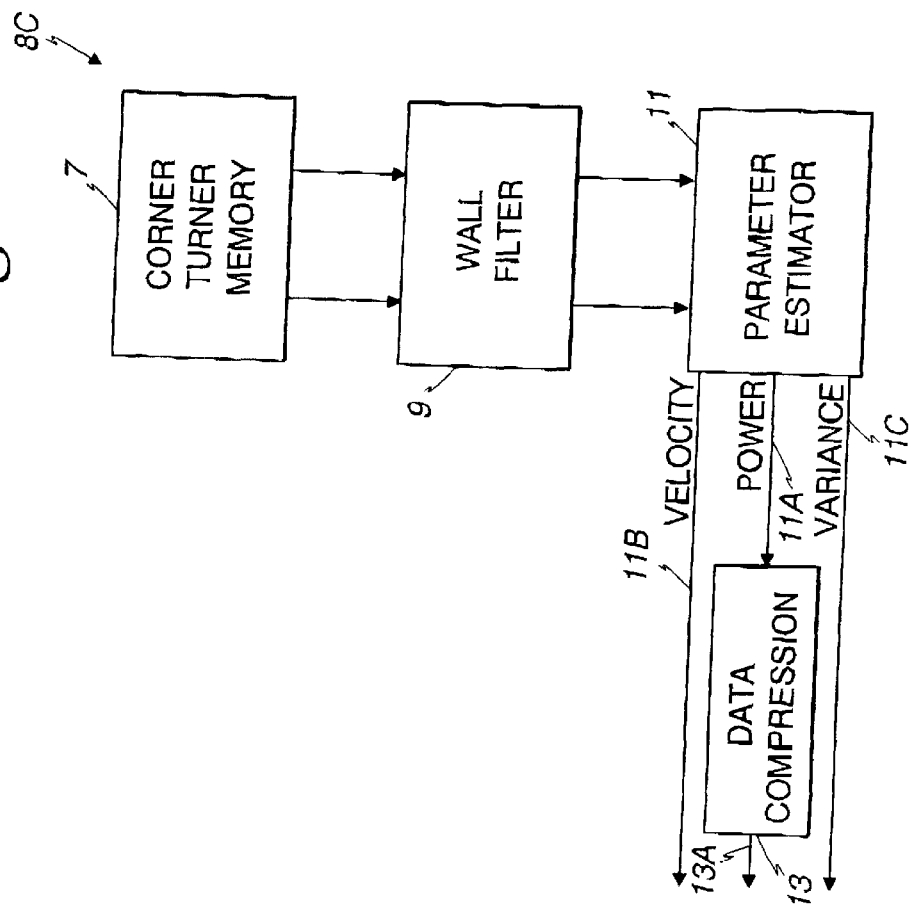
FIG. 2 is a schematic block diagram showing the mid processor color flow apparatus illustrated in FIG. 1.

FIG. 2 illustrates mid-processor 8C. The I/Q signal components from demodulator 6 are stored in a corner turner memory 7, whose purpose is to buffer data from possibly interleaved firings and output the data as vectors of points across firings at a given range cell. Data is received in "fast time", or sequentially down range (along a vector) for each firing. The output of the corner turner memory is reordered into "slow time", or sequentially by firing for each range cell. The resultant "slow time" I/Q signal samples are passed through a wall filter 9 which rejects any clutter corresponding to a stationary or very slow-moving tissue. The filtered outputs are then fed into a parameter estimator 11, which converts the range cell information into the intermediate autocorrelation parameters, N, D and R(O). N and D are the numerator and denominator the autocorrelation equation, as shown below:

$$N = \sum_{i=1}^{M-1} (I_i Q_{i+1} - I_{i+1} Q_i) \quad (2)$$

$$D = \sum_{i=1}^{M-1} (I_i I_{i+1} + Q_i Q_{i+1}) \quad (3)$$

where $I_i$ and $Q_i$ are the demodulated, basebanded input data for firing i, and M is the number of firings in the packet. R(O) is approximated as a finite sum over the number of firings in a packet, as follows:

$$R(O) = \sum_{i=1}^{M-1} \frac{(I_i^2 + Q_i^2 + I_{i+1}^2 + Q_{i+1}^2)}{2} \quad (4)$$

A processor converts N and D into a magnitude and phase for each range cell. The equations used are as follows:

$$|R(T)| = \sqrt{N^2 + D^2} \quad (5)$$

$$\phi(R(T)) = \tan^{-1}\left[\frac{N}{D}\right] \quad (6)$$

The parameter estimator processes the magnitude and phase values into signals having values representing estimates of power, velocity and turbulence of variance which are transmitted on conductors 11A, and 11B and 11C, respectively. The phase is used to calculate the mean Doppler frequency, which is proportional to the velocity as shown below: R(O) and |R(T)| (magnitude) are used to estimate the turbulence.

The mean Doppler frequency in hertz is obtained from the phase of N and D and the pulse repetition from T:

$$\bar{f} = \frac{1}{2\pi T}\tan^{-1}\left[\frac{N}{D}\right] = \frac{1}{2\pi T}(\phi(R(T))) \quad (7)$$

The mean velocity is calculated using the Doppler shift equation below. Since θ, the angle is between the flow direction and the sampling direction, is not know, cos θ is assumed to be 1.0.

$$\bar{v} = \frac{\bar{f}}{f_0}\frac{c}{2\cos\phi} \quad (8)$$

Preferably, the parameter estimator does not calculate the mean Doppler frequency as an intermediate output, but calculates $\bar{v}$ directly from the phase output of the processor using a look-up table.

The turbulence may be calculated in the time domain as a second-order series expansion of the variance of the mean Doppler frequency. The time domain expression for turbulence involves calculating the zero-lag and one-lag autocorrelation functions. R(O) and R(T) respectively. The exact autocorrelation functions are approximated by finite sums over the known data in the number of firings in a packet:

$$\sigma^2 = \frac{2}{(2\pi T)^2}\left[1 - \frac{|R(T)|}{R(O)}\right] \quad (9)$$

The mean value signal θ (R(T)) is an estimate of the mean Doppler frequency shift of the flowing reflectors, which in turn is proportional to the mean blood flow velocity. The variance signal $\sigma^2$ indicates the frequency spread of the flow signal component of the baseband echo signal. This value is indicative of flow turbulence, since laminar flow has a very narrow range of velocities, while turbulent flow is a mixture of many velocities. To indicate the strength of the signal from the flowing reflectors, the signal R(O) indicates the amount of the returned power in the Doppler-shifted flow signal.

The signal power on conductor 11A is passed through a data compression module 13 which compresses the data according to families of data compression curves. A different family of curves can be provided for different scanning applications. For example, one family of curves is provided for renal scanning, while another family of curves is provided for carotid artery scanning. Typically, there are about three curves per family. The dynamic range of the signals is changed according to the curve used for the data compression. The curves in each family are arranged in order of increasing dynamic range. Controller 26 sets the default curve when a user selects the scan application. The dynamic range controls the range of intensities or lumens created on display 18.

Figure 3:
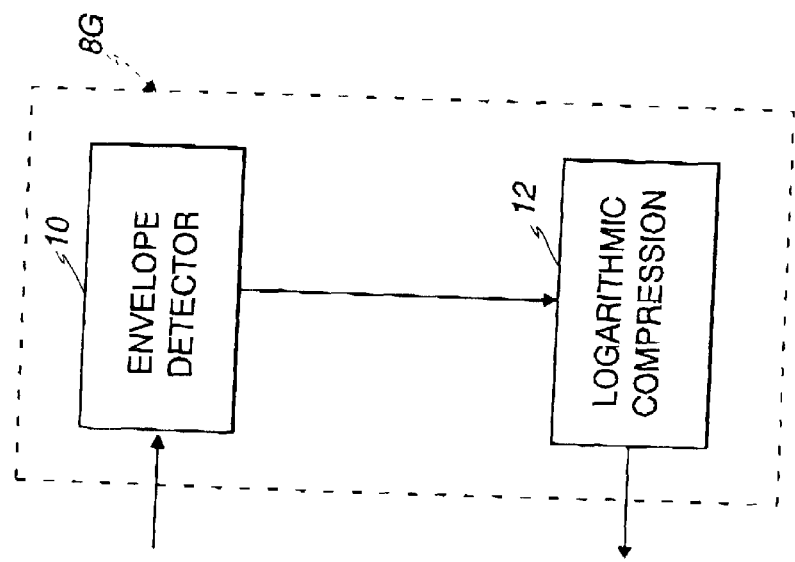
FIG. 3 is a schematic block diagram showing the mid processor B-mode apparatus illustrated in FIG. 1.

Referring to FIG. 3, gray scale B-mode mid-processor 8G includes an envelope detector 10 for forming the envelope of the beamsummed receive signal by commuting the quantity $(I^2+Q^2)^{1/2}$. The envelope of the signal undergoes some additional B-mode processing, such as logarithmic compression (block 12 in FIG. 3), to form display data which is output to the scan converter 14 (FIG. 1).

Referring again to FIG. 1, the color flow estimates and gray scale display data are sent to the scan converter 14, which converts the data into X-Y format for video display. The scan-converter frames are passed to a video processor 16, which basically maps the video data to a display color map and gray scale mage frames for video display. The image frames are then sent to the video monitor 18 for display. Typically, for color images, either velocity or power are displayed alone or velocity is displayed in conjunction with either power or turbulence. System control is centered in a host computer (not shown), which accepts operator inputs through an operator interface (e.g., a keyboard) and in turn controls the various subsystems.

In general, for B-mode gray scale images, the display data is converted by the scan converter 14 into X-Y format for video display. The scan-converted frames are passed to the video processor 16, which maps the video data to a gray scale or mapping for video display. The gray scale image frames are then sent to the video monitor 18 for display.

The images displayed by the video monitor 18 are produced from an image frame of data in which each datum indicates the intensity or brightness of a respective pixel in the display. An image frame may, e.g., comprise a 256×256 data array in which each intensity datum is an 8-bit binary number that indicates pixel brightness. The brightness of each pixel on the display monitor 18 is continuously refreshed by reading the value of its corresponding element in the data array in a well-known manner. Each pixel has an intensity value which is a function of the backscatter cross section of a respective sample volume in response to interrogating ultrasonic pulses and the gray map employed.

Figure 4:
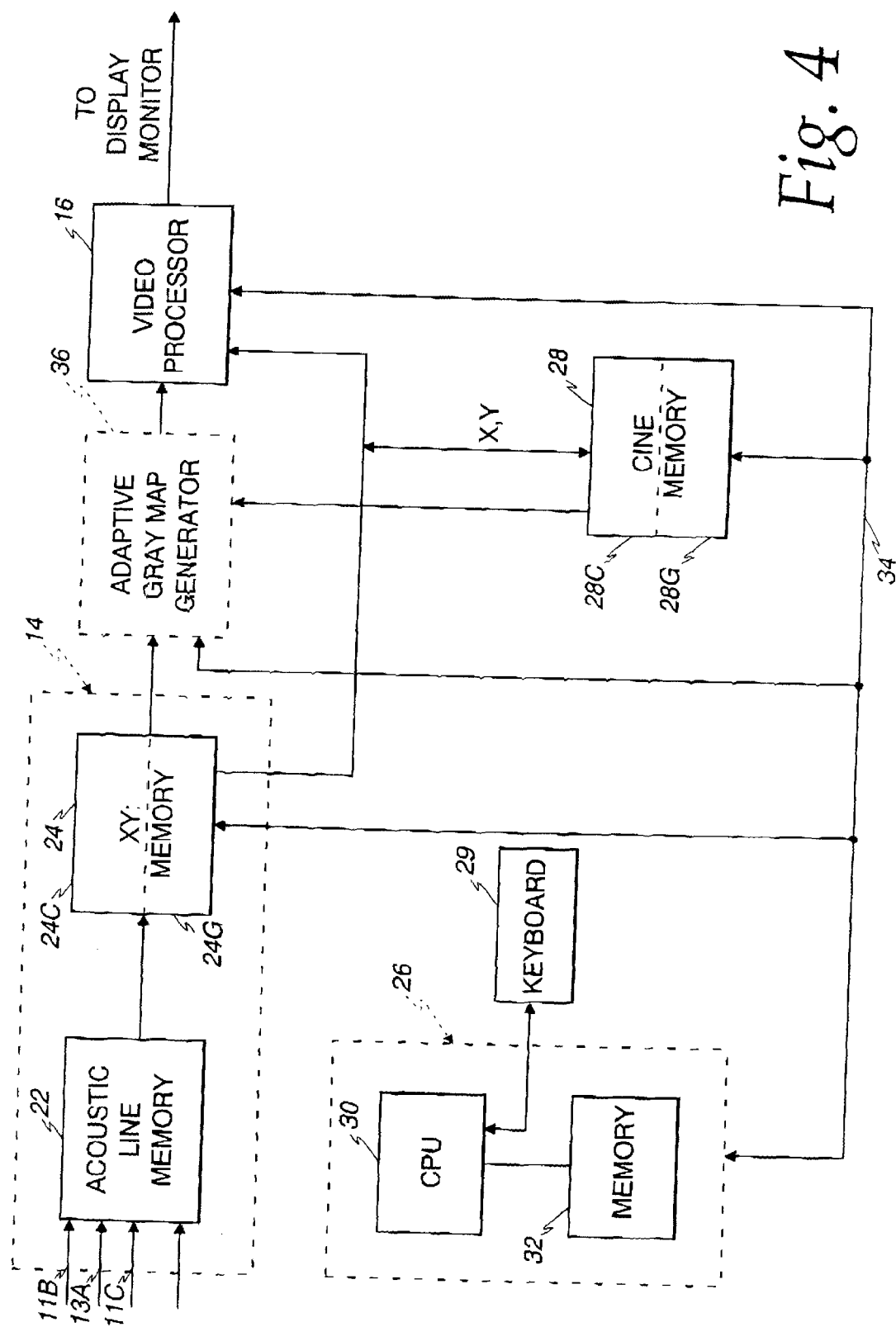
FIG. 4 is a schematic block diagram showing additional details of portions of the system illustrated in FIG. 1.

Referring to FIG. 4 system control is centered in a master controller or host computer 26, which accepts operator inputs through an operator interface (not shown) and in turn controls the various subsystems. The master controller 26 also generates the system timing and control signals. The master controller 26 comprises a central processing unit (CPU) 30 and a random access memory 32. A keyboard 29 is used to enter data into CPU 30. The CPU 30 has read only memory incorporated therein for storing routines used in constructing gray and color maps based on acquired raw data.

The scan converter 14 comprises an acoustic line memory 22 and an X-Y memory 24. The B-mode and color mode intensity data stored in polar coordinate (R-θ) sector format in acoustic line memory 22 is transformed to appropriately scaled Cartesian coordinate pixel display data, which is stored in X-Y memory 24. The color data is stored in memory locations 24C, and the gray scale data is stored in memory locations 24G. The scan-converted frames are passed to video processor 16, which maps the data to a gray map for video display. The gray scale image frames are then sent to the video monitor for display.

Successive frames of acoustic sample data are stored in cine memory 28 on a first-in, first-out basis. Color frames are stored in memory locations 28C and gray scale frames are stored in memory locations 28G. In the color region of interest, for every word of color data corresponding to a display pixel, there is a corresponding word of B-mode gray scale data corresponding to that pixel. The cine memory is like a circular image buffer that runs in the background, continually capturing acoustic sample data that is displayed in real time to the user. When the user freezes the system, the user has the capability to view acoustic sample data previously captured in cine memory.

The CPU 30 controls the XY memory 24 and the cine memory 28 via the system control bus 34. In particular, the CPU 30 controls the flow of raw data from the XY memory 24 to the video processor 16 and to the cine memory 28 and from the cine memory to the video processor 16 and to the CPU 26 itself. The CPU also loads the gray maps and color maps into the video processor.

Image frames are collected in cine memory 28 on a continuous basis. The cine memory 28 provides resident digital image storage for single image review and multiple image loop review and various control functions. The region of interest displayed during single-image cine replay is that used during the image's acquisition. The cine memory also acts as a buffer for transfer of images to digital archival devices (not shown) via the master controller 26.

The CPU 30 has random access memory for storing routines used in acquiring a raw data histogram, determining the end points of a new gray map input range, constructing a new gray map based on the end points of the new gray map input range, comparing the slope and gain of the new gray map to predetermined slope and gain limits, and if either limit is exceeded, reconstructing the new gray map to conform to the limit or limits.

In accordance with the preferred embodiments of the invention, the contrast of the ultrasound images is adjusted by the master controller 26 by creating a mapping of raw acoustic sample data into adjusted gray and color map values. First, the master controller 26 retrieves one or more image frames of raw data from the X-Y memory 24 or from the cine memory 28, storing that raw data in memory 32. The CPU 30 then compiles a histogram of the number of acoustic samples having an amplitude or value within each of a multiplicity of prescribed ranges or bins for the retrieved image frames of raw data.

According to the preferred embodiment, a color flow auto display processing mode is initiated by the user through keyboard 29 (FIG. 4) and can then be re-initiated by the user for updating of post-processing parameters or turned off altogether as the scanning situation changes.

The preferred embodiment uses the above-described B-mode gray scale and color flow scan data to optimize image quality of the color display. A composite histogram (histogram of the data over several frames) and/or a single frame histogram are constructed from the cine memory 28 data for color flow and/or B-mode by controller 26. Algorithms then are applied to the histogram results by controller 26 to determine how to properly adjust various parameters for a specific scanning situation or application.

By operating keyboard 29, the user may select the power only mode of color flow display (i.e., the PDI mode). According to the preferred embodiment, in the PDI mode, several discrete families of color flow dynamic range selections and data for corresponding compression curves are entered into memory 32 (FIG. 4). There is one family for each type of scanning application. For example, one family of dynamic range selections is used for ultrasound examination of the kidney, whereas another family of dynamic range selections is used for ultrasound examination of the carotid artery. In each family, there are three dynamic ranges available for automatic selection by the system. Each dynamic range is controlled by a different compression curve defined by digital data in memory 32.

The user enters the type of application on keyboard 29. In response, controller 26 presets the middle value dynamic range selection and corresponding compression curve which represents the typical dynamic range encountered when scanning the application selected by the user. The lower dynamic range in the family provides less dynamic range and the higher dynamic range in the family provides increased dynamic range compared to the middle dynamic range setting. Using the families of dynamic ranges, the auto dynamic range selection algorithm part of the auto color flow display processing mode automated dynamic range selection.

First, n frames of PDI color flow data are collected from cine memory 28C which represents the amplitude of the flow data present in the color flow region of interest (ROI) using the current preset dynamic range setting and compression curve. The n frames of data are required to account for flow pulsatility. Controller 26 executes the auto dynamic range selection algorithm which generates a first composite histogram of the data.

Figure 5:
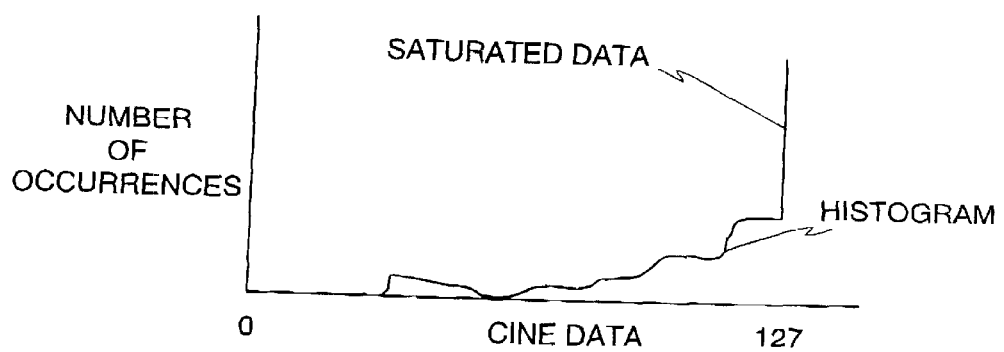
FIG. 5 is a graph illustrating one possible form of data stored in the cine memory shown in FIG. 4.

In the event the preset dynamic range is too low, a substantial percent of the data may be saturated at the maximum output value of 127. That is, the values are clustered in a range which is too high to create an optimum image on display monitor 18. Such a condition results in a first histogram of the type shown in FIG. 5. The auto dynamic range selection algorithm analyzes the first histogram, and, if at least x percent of the data is saturated at the maximum output value of 127 (i.e., condition 1 which is illustrated in FIG. 5), then the dynamic range is flagged as being too low, and the next higher dynamic range and corresponding compression curve stored in memory 32 are selected.

Figure 6:
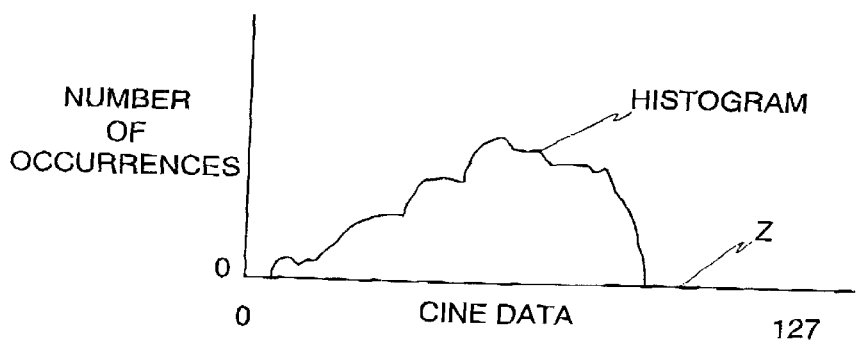
FIG. 6 is a graph showing another possible form of data stored in the cine memory shown in FIG. 4.

In the event the present dynamic range is too high, all of the data have values substantially below the maximum output value of 127. That is, all of the values are clustered in a range which is too low to create an optimum image on display monitor 18. Such a condition results in a first histogram of the type shown in FIG. 6. The auto dynamic range selection algorithm analyzes the first histogram, and, if less than t percent of the data occurs at output values between z and the maximum value of 127 (i.e., condition 2 which is illustrated in FIG. 6), then the dynamic range is flagged as being too high, and the next lower dynamic range and corresponding compression curve stored in memory 32 are selected.

Figure 7:
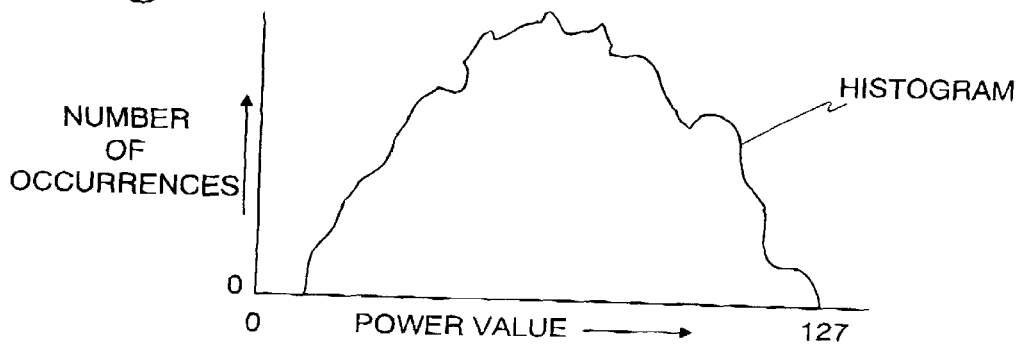
FIG. 7 is a graph showing another possible form of data resulting from use of the preferred form of the invention.

Based on the newly selected dynamic range and compression curve, the auto dynamic range selection algorithm calculates a second histogram based on the same data used to calculate the first histogram. The original dynamic range and compression curve are used to decompress the original data. The original data then is applied to the newly selected dynamic range and compression curve to create new compressed data in memory 32. The second histogram calculated from the new compressed data using the new dynamic range typically shows a spread of values more appropriate for optimum viewing on display monitor 18. Such an exemplary second histogram may be of the type shown in FIG. 7.

Alternatively, of more than three dynamic ranges and three compression curves per family are provided, the process may be repeated as new dynamic ranges and compression curves are selected. If the first histogram showed that the dynamic range was too low (i.e., condition 1 shown in FIG. 5), the process of selecting dynamic ranges and compression curves, decompressing the data, compressing the data using the newly selected curve and calculating second and subsequent histograms is repeated until y percent of the data or less is determined to be saturated (the condition shown in FIG. 7) or until the highest dynamic range setting is reached, effectively spreading the data out over more of the lower output values. If the original histogram showed that the dynamic range was too high (i.e., condition 2 shown in FIG. 6), the process of selecting dynamic ranges and compression curves, decompressing the data, compressing the data using the newly selected curve and calculating second and subsequent histograms is repeated until q percent of the data or more is determined to be between z and 127 (the condition shown in FIG. 7) or until the lowest dynamic range setting is reached, effectively, spreading the data out over more of the higher output values.

As a second alternative, the first histogram may be used to calculate a new compression curve not previously stored which more nearly spreads the actual data over the dynamic range available for display. The new compression curve then is used to recompress the original data.

If neither condition 1 nor condition 2 is met, then the current dynamic range and compression curve are maintained.

As an alternative to the preceding steps, controller 26 forms a histogram of the PDI data before any dynamic range compression is applied or uncompresses the data and forms a histogram. Then the histogram of uncompressed PDI data is analyzed to determine its statistics, and an optimal dynamic range compression scheme is calculated. Various dynamic range compression curves such as logarithmic, cube root, S-curve, or others are optimally applied across the data based on the statistics of the histogram. This alternative preferably is implemented by a digital signal processor (DSP).

The user can choose to re-activate the color flow auto display processing mode, causing new data to be formed into a histogram, based on the current dynamic range setting, and causing the auto dynamic range selection algorithm to be re-employed. Or the user can turn off the color flow auto display processing mode, causing the current dynamic range setting to be maintained until the user changes the selection manually.

The embodiments described here can be extended to automatically adjust other post-processing parameters such as power threshold, wall filter cutoffs, baseline shifts, and velocity scales. The same basic idea of collecting B and/or color flow frames of cine data would be applied and associated algorithms would be employed to determine exactly how to adjust the particular post processing parameter.

Figure 8:
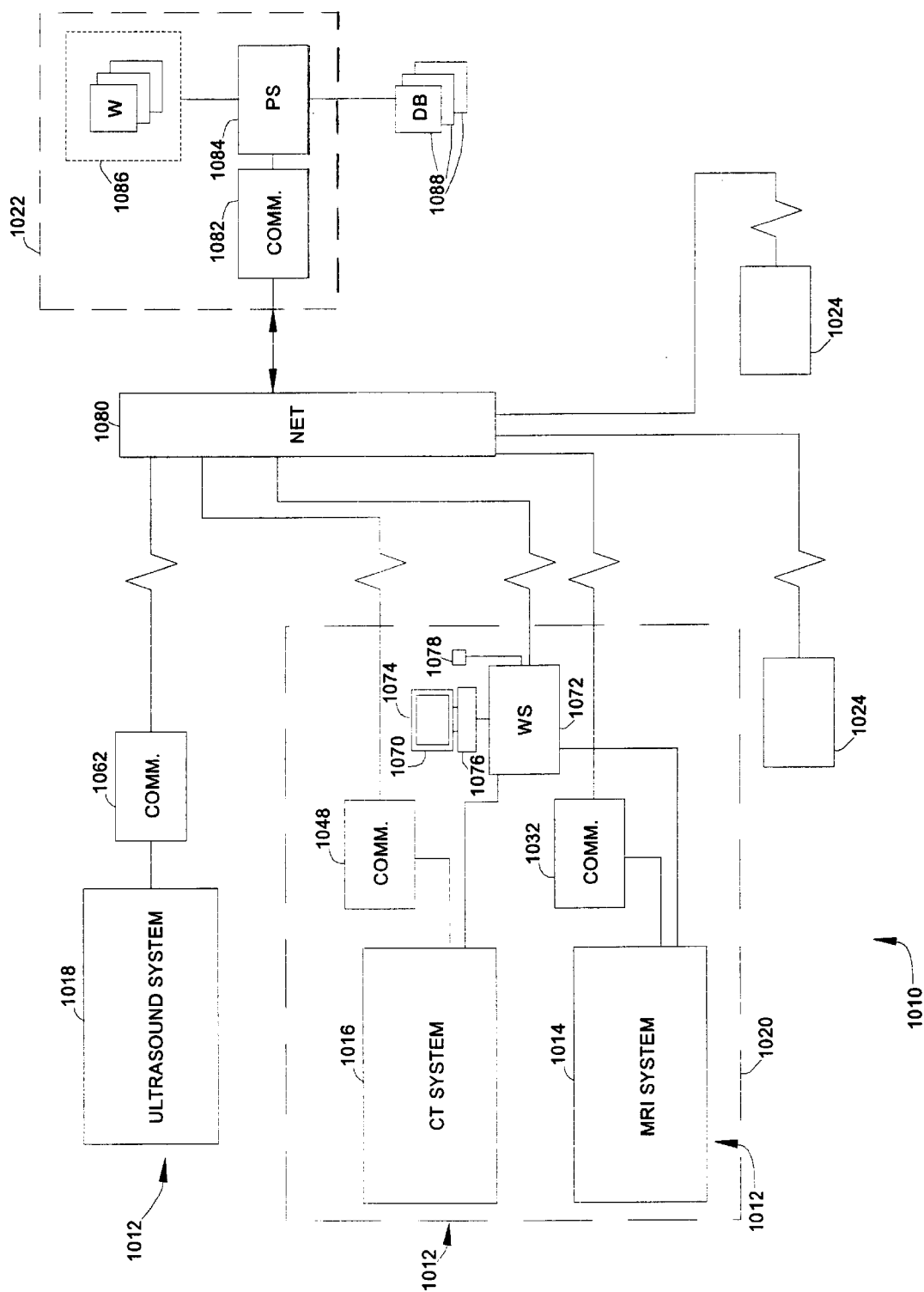
FIG. 8 is a diagrammatical representation of a series of medical diagnostic systems coupled to a service facility via a network connection for providing remote services and data interchange between the diagnostic systems and the service facility.

Referring now to FIG. 8, a service system 1010 is illustrated for providing remote service to a plurality of medical diagnostic systems 1012. In the embodiment illustrated in FIG. 8, the medical diagnostic systems include a magnetic resonance imaging (MRI) system 1014, a computed tomography (CT) system 1016, and an ultrasound imaging system 1018. The diagnostic systems may be positioned in a single location or facility, such as a medical facility 1020, or may be remote from one another as shown in the case of ultrasound system 1018. The diagnostic systems are serviced from a centralized service facility 1022. Moreover, a plurality of field service units 1024 may be coupled in the service system for transmitting service requests, verifying service status, transmitting service data and so forth as described more fully below.

In the exemplary embodiment of FIG. 8, several different system modalities are provided with remote service by the service facility. Remote services include but are not limited to services, such as, remote monitoring, remote system control, immediate file access from remote locations, remote file storage and archiving, remote resource pooling, remote recording, and remote high speed computations. Remote services are provided to a particular modality depending upon the capabilities of the service facility, the types of diagnostic systems subscribing to service contracts with the facility, as well as other factors.

Depending upon the modality of the systems, various subcomponents or subsystems will be included. In the case of MRI system 1014, such systems will generally include a scanner, a control and signal detection circuit, a system controller, and an operator station. MRI system 1014 includes a uniform platform for interactively exchanging service requests, messages and data with service facility 1022 as described more fully below. MRI system 1014 is linked to a communications module 1032, which may be included in a single or separate physical package from MRI system 1014. In a typical system, additional components may be included in system 1014, such as a printer or photographic system for producing reconstructed images based upon data collected from the scanner.

Similarly, CT system 1016 will typically include a scanner, a signal acquisition unit, and a system controller. The scanner detects portions of x-ray radiation directed through a subject of interest. The controller includes circuitry for commanding operation of the scanner and for processing and reconstructing image data based upon the acquired signals. CT system 1016 is linked to a communications module 1048 for transmitting and receiving data for remote services. Moreover, like MRI system 1014, CT system 1016 will generally include a printer or similar device for outputting reconstructed images based upon data collected by the scanner.

In the case of ultrasound system 1018, such systems will generally include a scanner and data processing unit and a system controller. Ultrasound system 1018 is coupled to a communications module 1062 for transmitting service requests, messages and data between ultrasound system 1018 and service facility 1022.

Although reference is made herein generally to "scanners" in diagnostic systems, that term should be understood to include medical diagnostic data acquisition equipment generally, not limited to image data acquisition, as well as to picture archiving communications and retrieval systems, image management systems, facility or institution management systems, viewing systems and the like, in the field of medical diagnostics.

Where more than one medical diagnostic system is provided in a single facility or location, as indicated in the case of MRI and CT systems 1014 and 1016 in FIG. 8, these may be coupled to a management station 1070, such as in a radiology department of a hospital or clinic. The management station may be linked directly to controllers for the various diagnostic systems. The management system may include a computer workstation or personal computer 1072 coupled to the system controllers in an intranet configuration, in a file sharing configuration, a client/server arrangement, or in any other suitable manner. Moreover, management station 1070 will typically include a monitor 1074 for viewing system operational parameters, analyzing system utilization, and exchanging service requests and data between the facility 1020 and the service facility 1022. Input devices, such as a standard computer keyboard 1076 and mouse 1078, may also be provided to facilitate the user interface.

It should be noted that, alternatively, the management system, or other diagnostic system components, may be "stand-alone" or not coupled directly to a diagnostic system. In such cases, the service platform described herein, and some or all of the service functionality nevertheless be provided on the management system. Similarly, in certain applications, a diagnostic system may consist of a stand-alone or networked picture archiving communications and retrieval system or a viewing station provided with some or all of the functionality described herein.

The communication modules mentioned above, as well as workstation 1072 and field service units 1024 may be linked to service facility 1022 via a remote access network 1080. For this purpose, any suitable network connection may be employed. Presently preferred network configurations include both proprietary or dedicated networks, as well as open networks, such as the Internet. Data may be exchanged between the diagnostic systems, field service units, and remote service facility 1022 in any suitable format, such as in accordance with the Internet Protocol (IP), the Transmission Control Protocol (TCP), or other known protocols. Moreover, certain of the data may be transmitted or formatted via markup languages such as the HyperText Markup Language (HTML), or other standard languages. The presently preferred interface structures and communications components are described in greater detail below.

Within service facility 1022, messages, service requests and data are received by communication components as indicated generally at reference numeral 1082. Components 1082 transmit the service data to a service center processing system, represented generally at reference numeral 1084 in FIG. 8. The processing system manages the receipt, handling and transmission of service data to and from the service facility. In general, processing system 1084 may include one or a plurality of computers, as well as dedicated hardware or software servers for processing the various service requests and for receiving and transmitting the service data as described more fully below.

Service facility 1022 also includes a bank of operator workstations 1086 which may be staffed by personnel who address the service requests and provide off and on-line service to the diagnostic systems in response to the service requests. Also, processing system 1084 may be linked to a system of databases or other processing systems 1088 at or remote from the service facility 1022. Such databases and processing systems may include extensive database information on operating parameters, service histories, and so forth, both for particular subscribing scanners, as well as for extended populations of diagnostic equipment.

Figure 9:
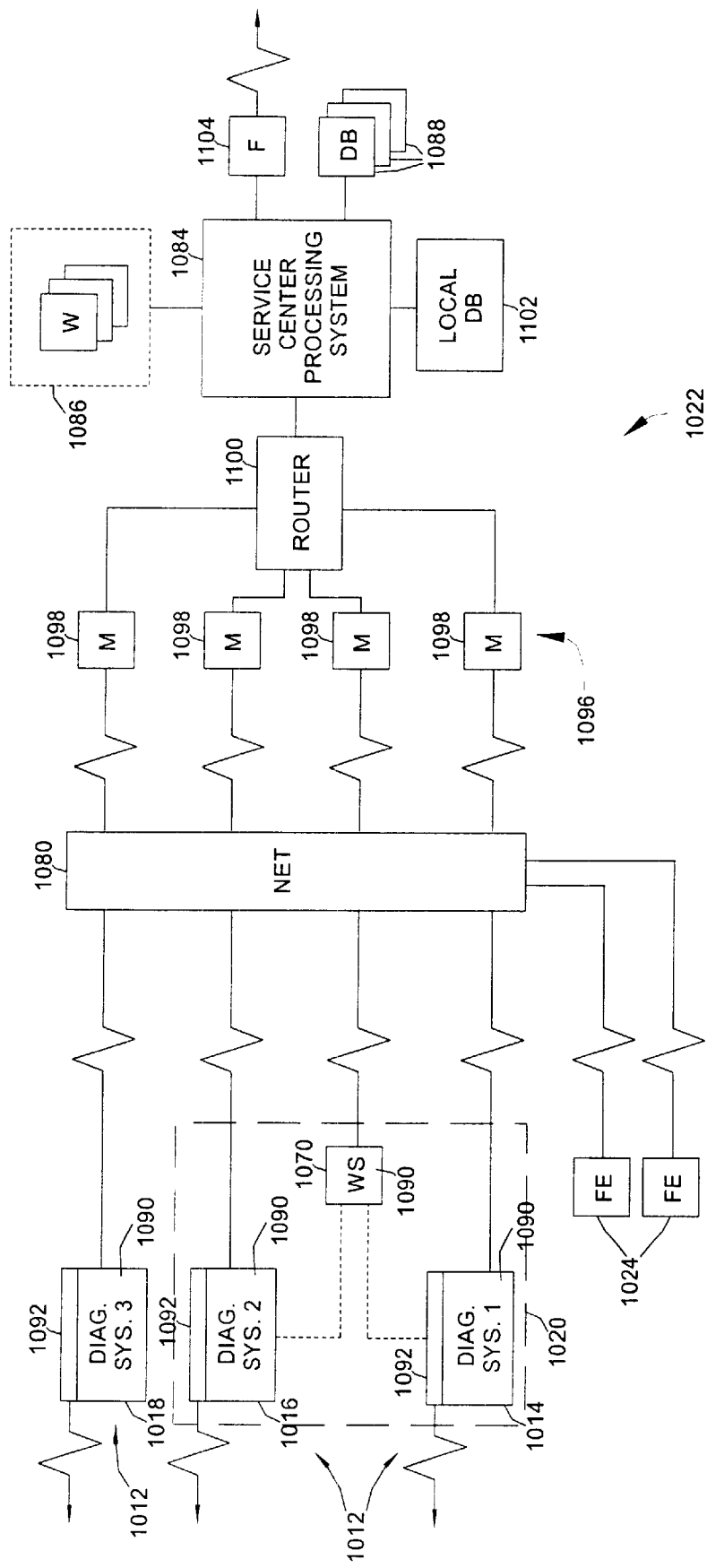
FIG. 9 is a block diagram of the systems shown in FIG. 8 illustrating certain functional components of the diagnostic systems and the service facility.

FIG. 9 is a block diagram illustrating the foregoing system components in a functional view. As shown in FIG. 9, the field service units 1024 and the diagnostic systems 1012 can be linked to the service facility 1022 via a network connection as illustrated generally at reference numeral 1080. Within each diagnostic system 1012, a uniform service platform 1090 is provided.

Platform 1090, which is described in greater detail below with particular reference to FIG. 10, includes hardware, firmware, and software components adapted for composing service requests, transmitting and receiving service data, establishing network connections and managing financial or subscriber arrangements between diagnostic systems and the service facility. Moreover, the platforms provide a uniform graphical user interface at each diagnostic system, which can be adapted to various system modalities to facilitate interaction of clinicians and radiologists with the various diagnostic systems for service functions. The platforms enable the scanner designer to interface directly with the control circuitry of the individual scanners, as well as with memory devices at the scanners, to access image, log and similar files needed for rendering requested or subscribed services. Where a management station 1070 is provided, a similar uniform platform is preferably loaded on the management station to facilitate direct interfacing between the management station and the service facility. In addition to the uniform service platform 1090, each diagnostic system is preferably provided with an alternative communications module 1092, such as a facsimile transmission module for sending and receiving facsimile messages between the scanner and remote service facilities.

Messages and data transmitted between the diagnostic systems and the service facility traverse a security barrier or "firewall" contained within processing system 1084 as discussed below, which prevents unauthorized access to the service facility in a manner generally known in the art. A modem rack 1096, including a series of modems 1098, receives the incoming data, and transmits outgoing data through a router 1100 which manages data traffic between the modems and the service center processing system 1084.

In the diagram of FIG. 9, operator workstations 1086 are coupled to the processing system, as are remote databases or computers 1088. In addition, at least one local service database 1102 is provided for verifying license and contract arrangements, storing service record files, log files, and so forth. Moreover, one or more communication modules 1104 are linked to processing system 1084 to send and receive facsimile transmissions between the service facility and the diagnostic systems or field service units.

Figure 10:
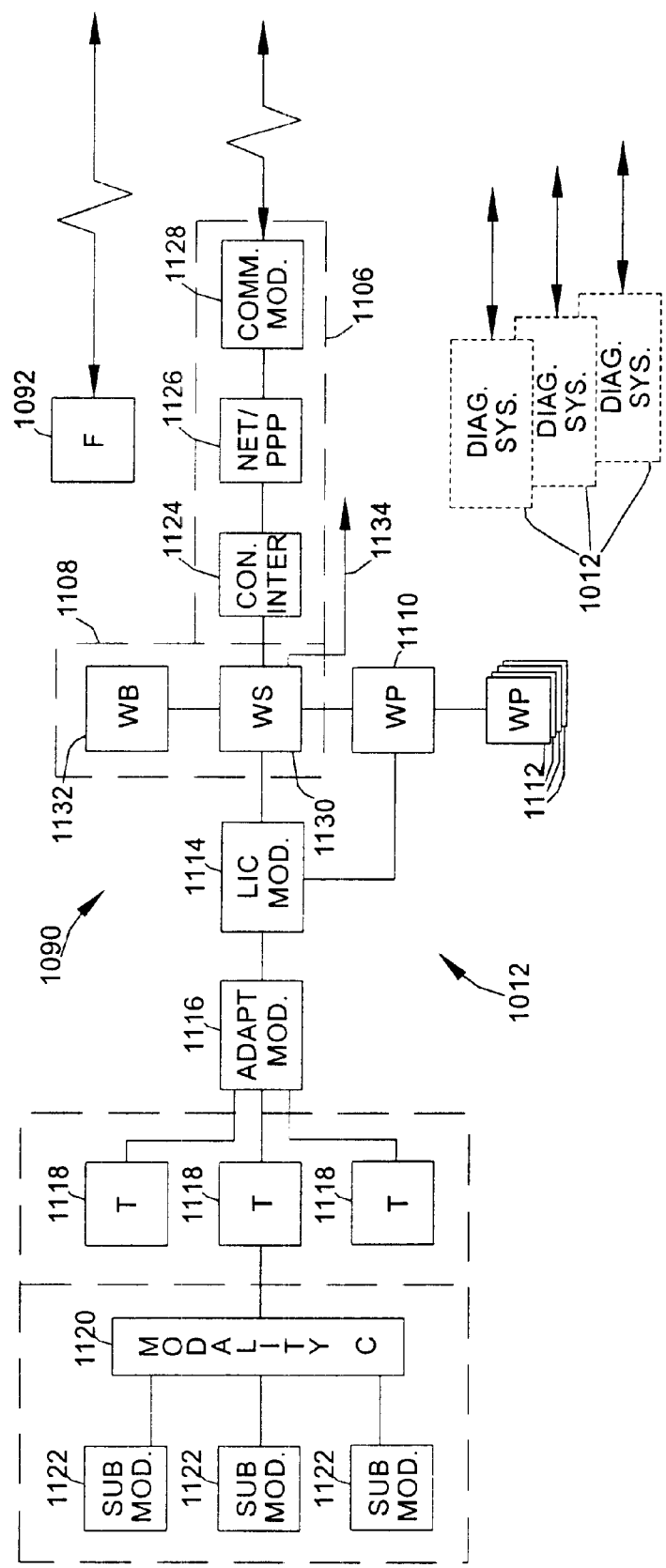
FIG. 10 is a block diagram of certain functional components within a diagnostic system of the type shown in FIG. 8 and FIG. 9 for facilitating interactive remote servicing of the diagnostic system.

FIG. 10 illustrates diagrammatically the various functional components comprising the uniform service platform 1090 within each diagnostic system 1012. As shown in FIG. 10, the uniform platform includes a device connectivity module 1106, as well as a network connectivity module 1108. Network connectivity module 1108 accesses a main web page 1110 which, as mentioned above, is preferably a markup language page, such as an HTML page displayed for the system user on a monitor at the diagnostic system. Main web page 1110 is preferably accessible from a normal operating page in which the user will configure examination requests, view the results of examinations, and so forth such as via an on-screen icon. Through main web page 1110, a series of additional web pages 1112 are accessible. Such web pages permit remote service requests to be composed and transmitted to the remote service facility, and facilitate the exchange of other messages, reports, software, protocols, and so forth as described more fully below.

It should be noted that as used herein the term "page" includes a user interface screen or similar arrangement which can be viewed by a user of the diagnostic system, such as screens providing graphical or textual representations of data, messages, reports and so forth. Moreover, such pages may be defined by a markup language or a programming language such as Java, perl, java script, or any other suitable language.

Network connectivity module 1108 is coupled to a license module 1114 for verifying the status of license, fee or contractual subscriptions between the diagnostic system and the service facility. As used herein, the term "subscription" should be understood to include various arrangements, contractual, commercial or otherwise for the provision of services, information, software, and the like, both accompanies with or without payment of a fee. Moreover, the particular arrangements manages by systems as described below may include several different types of subscriptions, including time-expiring arrangements, one-time fee arrangements, and so-called "pay per use" arrangements, to mention but a few.

License module 1114 is, in turn, coupled to one or more adapter utilities 1116 for interfacing the browser, server, and communications components with modality interface tools 1118. In a presently preferred configuration, several such interface tools are provided for exchanging data between the system scanner and the service platform. For example, modality interface tools 1118 may include applets or servlets for building modality-specific applications, as well as configuration templates, graphical user interface customization code, and so forth. Adapters 1116 may interact with such components, or directly with a modality controller 1120 which is coupled to modality-specific subcomponents 1122.

The modality controller 1120 and modality-specific subcomponents 1122 will typically include a preconfigured processor or computer for executing examinations, and memory circuitry for storing image data files, log files, error files, and so forth. Adapter 1116 may interface with such circuitry to convert the stored data to and from desired protocols, such as between the HyperText Transfer Protocol (HTTP) and DICOM, a medical imaging standard for data presentation. Moreover, transfer of files and data as described below may be performed via any suitable protocol, such as a file transfer protocol (FTP) or other network protocol.

In the illustrated embodiment, device connectivity module 1106 includes several components for providing data exchange between the diagnostic system and the remote service facility. In particular, a connectivity service module 1124 provides for interfacing with network connectivity module 1108. A Point-to-Point Protocol (PPP) module 1126 is also provided for transmitting Internet Protocol (IP) packets over remote communication connections. Finally, a modem 1128 is provided for receiving and transmitting data between the diagnostic system and the remote service facility. As will be appreciated by those skilled in the art, various other network protocols and components may be employed within device connectivity module 1106 for facilitating such data exchange.

Network connectivity module 1108 preferably includes a server 1130 and a browser 1132. Server 1130 facilitates data exchange between the diagnostic system and the service facility, and permits a series of web pages 1110 and 1112 to be viewed via browser 1132. In a presently preferred embodiment, server 1130 and browser 1132 support HTTP applications and the browser supports java applications. Other servers and browsers, or similar software packages may, of course, be employed for exchanging data, service requests, messages, and software between the diagnostic system, the operator and the remote service facility. Finally, a direct network connection 1134 may be provided between server 1130 and an operator workstation, such as management station 1070 within the medical facility (see FIGS. 8 and 9).

In a present embodiment, the components comprising network connectivity module may be configured via an application stored as part of the uniform platform. In particular, a Java application licensed to a service engineer enables the engineer to configure the device connectivity at the diagnostic system to permit it to connect with the service facility.

Figure 11:
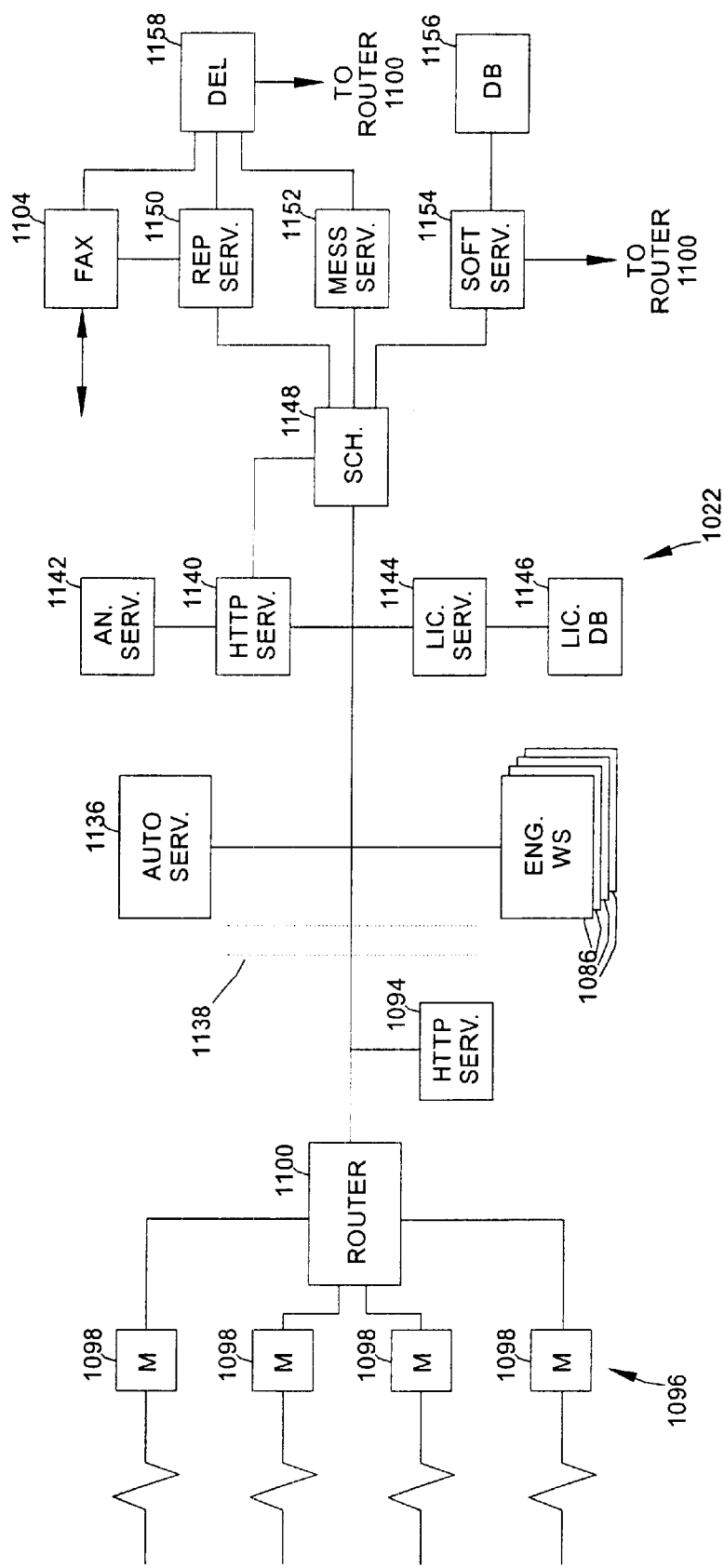
FIG. 11 is a block diagram of certain of the functional components of the service facility illustrated in FIG. 8 and FIG. 9 for rendering interactive remote service to a plurality of medical diagnostic systems.

FIG. 11 illustrates exemplary functional components for service facility 1022. As indicated above, service facility 1022 includes a modem rack 1096 comprising a plurality of modems 1098 coupled to a router 1100 for coordinating data communications with the service facility. An HTTP service server 1094 receives and directs incoming and outgoing transactions with the facility. Server 1094 is coupled to the other components of the facility through a firewall 1138 for system security. Operator workstations 1086 are coupled to the port manager for handling service requests and transmitting messages and reports in response to such requests.

An automated service unit 1136 may also be included in the service facility for automatically responding to certain service requests, sweeping subscribing diagnostic systems for operational parameter data, and so forth, as described below. In a presently preferred embodiment, the automated service unit may operate independently of or in conjunction with the interactive service components comprising processing system 1084. It should be noted that other network or communications schemes may be provided for enabling the service facility to communicate and exchange data and messages with diagnostic systems and remote service units, such as systems including outside Internet service providers (ISP's), virtual private networks (VPN's) and so forth.

Behind firewall 1138, an HTTP application server 1140 coordinates handling of service requests, messaging, reporting, software transfers and so forth. Other servers may be coupled to HTTP server 1140, such as service analysis servers 1142 configured to address specific types of service requests, as described more fully below. In the illustrated embodiment, processing system 1084 also includes a license server 1144 which is coupled to a license database 1146 for storing, updating and verifying the status of diagnostic system service subscriptions. Alternatively, where desired, license server 1144 may be placed outside of fire wall 1138 to verify subscription status prior to admission to the service facility.

Handling of service requests, messaging, and reporting is further coordinated by a scheduler module 1148 coupled to HTTP server 1140. Scheduler module 1148 coordinates activities of other servers comprising the processing system, such as a report server 1150, a message server 1152, and a software download server 1154. As will be appreciated by those skilled in the art, servers 1150, 1152 and 1154 are coupled to memory devices (not shown) for storing data such as addresses, log files, message and report files, applications software, and so forth. In particular, as illustrated in FIG. 11, software server 1154 is coupled via one or more data channels to a storage device 1156 for containing transmittable software packages which may be sent directly to the diagnostic systems, accessed by the diagnostic systems, or supplied on pay-per-use or purchase basis. Message and report servers 1152 and 1150 are further coupled, along with communications module 1104, to a delivery handling module 1158, which is configured to receive outgoing messages, insure proper connectivity with diagnostic systems, and coordinate transmission of the messages.

In a presently preferred embodiment, the foregoing functional circuitry may be configured as hardware, firmware, or software on any appropriate computer platform. For example, the functional circuitry of the diagnostic systems may be programmed as appropriate code in a personnel computer or workstation either incorporated entirely in or added to the system scanner. The functional circuitry of the service facility may include additional personal computers or workstations, in addition to a main frame computer in which one or more of the servers, the scheduler, and so forth, are configured. Finally, the field service units may comprise personal computers or laptop computers of any suitable processor platform. It should also be noted that the foregoing functional circuitry may be adapted in a variety of manners for executing the functions described herein. In general, the functional circuitry facilitates the exchange of remote service data between the diagnostic systems and a remote service facility, which is preferably implemented in an interactive manner to provide regular updates to the diagnostic systems of service activities.

As described above, both the diagnostic systems and the field service units preferably facilitate interfacing between a variety of diagnostic system modalities and the remote service facility via a series of interactive user-viewable pages. Exemplary pages include capabilities of providing interactive information, composing service requests, selecting and transferring messages, reports and diagnostic system software, and so forth. Pages facilitate the interaction and use of remote services, such as, remote monitoring, remote system control, immediate file access from remote locations, remote file storage and archiving, remote resource pooling, remote recording, and remote high speed computations.

The user can access specific documents described in text areas of the pages by selection of all or a portion of the text describing the documents. In the presently preferred embodiment, the accessed documents may be stored in local memory devices within the diagnostic system, or selection of the text may result in loading of a uniform resource locator (URL) for accessing a remote computer or server via a network link.

Advantageously, service system 1010 (FIG. 8) provides remote services, such as, remote upgrades, remote diagnostics, remote servicing, remote viewing, remote file storage, remote control, and remote adjustments to system parameters and functions. Furthermore, remote services provide for contractual arrangements, such as, per use licenses which lease the medical diagnostic equipment based on use. Additionally, remote services may include expert on-line assistance for image scanning techniques, image analysis, pathology detection, imaging unit maintenance, and other expert-aided operations.

While the embodiments illustrated in the Figures and described above are presently preferred, it should be understood that the embodiments are offered by way of example only. Other embodiments may include enhanced remote features made possible by the network structures and functionalities described herein. The invention is not limited to a particular embodiment, but extends to various modifications, combinations, and permutations that nevertheless fall within the scope and spirit of the appended claims.

What is claimed is:

1. An ultrasound imaging system for generating color flow signals in response to ultrasound signals backscattered from a subject under study, the system including an apparatus for displaying images in response to the color flow signals comprising in combination:

a memory connected to store first memory values in response to the color flow signals;

a logic unit connected to determine a dynamic range compression scheme based on an analysis of the first memory values and to generate second memory values based on the dynamic range compression scheme;

a display connected to display a color flow image in response to the second memory values; and a network connectivity module coupled to the system to provide communication with a remote facility over a network, the remote facility providing remote services.

2. Apparatus, as claimed in claim 1, wherein the first memory values are altered from the values of the color flow signals based on a second dynamic range compression scheme.

3. Apparatus, as claimed in claim 1, wherein the logic unit is connected to create the dynamic range compression scheme based on an algorithm which analyzes the first memory values.

4. Apparatus, as claimed in claim 1, wherein the first memory values equal the values of the color flow signals.

5. Apparatus, as claimed in claim 1, wherein the memory stores compression data defining first and second dynamic range compression schemes, wherein the logic unit determines the dynamic range compression scheme by selecting one of the first or second stored dynamic range compression schemes and wherein the first memory values are altered based on the selected dynamic range compression scheme.

6. Apparatus, as claimed in claim 5, wherein the first dynamic range compression scheme comprises a first type and the second dynamic ranges comprises a second type different from the first type.

7. Apparatus, as claimed in claim 5, wherein the first memory values are altered from the values of the color flow signals based on a third dynamic range compression scheme.

8. Apparatus, as claimed in claim 7, wherein the logic unit is connected to analyze the first memory values by decompressing the first memory values, analyzing the decompressed first memory values, selecting one of the first or second stored dynamic range compression schemes, altering the decompressed first memory values based on the selected dynamic range compression scheme to generate second memory values and enabling storage of the second memory values.

9. Apparatus, as claimed in claim 1, wherein the logic unit is connected to analyze the first memory values by generating a histogram of the first memory values.

10. Apparatus, as claimed in claim 1, wherein the first memory values represent power estimates calculated in response to the backscattered signals.

11. In an ultrasound imaging system generating color flow signals in response to ultrasound signals backscattered from a subject under study, an improved method for displaying images in response to the color flow signals comprising the steps of:

storing first memory values in response to the color flow signals; determining a dynamic range compression scheme based on an analysis of the first memory values;

generating second memory values based on the dynamic range compression scheme;

displaying a color flow image in response to the second memory values; and communicating the color flow image or data associated with the image to a remote facility, the remote facility providing remote services over a network.

12. A method, as claimed in claim 11, wherein the step of storing the first memory values comprises the step of altering the values of the color flow signals based on a second dynamic range compression scheme.

13. A method, as claimed in claim 11, wherein the step of determining a dynamic range compression scheme comprises the step of creating the dynamic range compression scheme by analyzing the first memory values.

14. A method, as claimed in claim 11, wherein the first memory values equal the values of the color flow signals.

15. A method, as claimed in claim 11, wherein the step of storing comprises the step of storing compression data defining first and second dynamic range compression schemes, wherein the step of determining a dynamic range compression scheme comprises the step of selecting one of the first or second stored dynamic range compression schemes and wherein the step of generating second memory values comprises the step of altering the values of the color flow signals based on the selected dynamic range compression scheme.

16. A method, as claimed in claim 15, wherein the first dynamic range compression scheme comprises a first type and the second dynamic ranges comprises a second type different from the first type.

17. A method, as claimed in claim 15, wherein the step of storing comprises the step of altering from the values of the color flow signals based on a third dynamic range compression scheme.

18. A method, as claimed in claim 17, wherein the step of selecting comprises the steps of:

decompressing the first memory values; and analyzing the decompressed first memory values.

19. A method, as claimed in claim 18, wherein the step of generating comprises the steps of:

altering the decompressed first memory values based on the selected dynamic range compression scheme to generate second memory values; and enabling storage of the second memory values.

20. A method, as claimed in claim 11, wherein the step of determining a dynamic range compression scheme comprises the step of analyzing the first memory values by generating a histogram of the first memory values.

21. A method, as claimed in claim 11, wherein the first memory values represent power estimates calculated in response to the backscattered signals.

* * * * *